United States Patent
Jiskoot et al.

(10) Patent No.: US 10,058,828 B2
(45) Date of Patent: Aug. 28, 2018

(54) APPARATUS FOR MIXING OF FLUIDS FLOWING THROUGH A CONDUIT

(71) Applicant: Cameron International Corporation, Houston, TX (US)

(72) Inventors: Mark A. Jiskoot, Tunbridge Wells (GB); James M. Baker, Tunbridge Wells (GB); Gary M. Potten, Houston, TX (US)

(73) Assignee: Cameron International Corporation, Houston, TX (US)

( * ) Notice: Subject to any disclaimer, the term of this patent is extended or adjusted under 35 U.S.C. 154(b) by 286 days.

(21) Appl. No.: 14/727,463

(22) Filed: Jun. 1, 2015

(65) Prior Publication Data

US 2016/0346744 A1    Dec. 1, 2016

(51) Int. Cl.
| | |
|---|---|
| *B01F 5/02* | (2006.01) |
| *B01F 5/04* | (2006.01) |
| *B01F 5/10* | (2006.01) |
| *B01F 3/00* | (2006.01) |
| *G01N 1/20* | (2006.01) |

(Continued)

(52) U.S. Cl.
CPC ........... *B01F 5/0275* (2013.01); *B01F 5/048* (2013.01); *B01F 5/0471* (2013.01); *B01F 5/0475* (2013.01); *B01F 5/0476* (2013.01); *B01F 5/0483* (2013.01); *B01F 5/0485* (2013.01); *B01F 5/0486* (2013.01); *B01F 5/10* (2013.01); *G01N 1/2035* (2013.01); *G01N 1/38* (2013.01); *B01F 15/0223* (2013.01); *B01F 15/0224* (2013.01); *B01F 15/0243* (2013.01); *B01F 2003/005* (2013.01); *B01F 2005/0005* (2013.01); *B01F 2005/0022* (2013.01); *B01F 2005/0034* (2013.01); *G01N 2001/205* (2013.01)

(58) Field of Classification Search
CPC ...... B01F 5/0471; B01F 5/0475; B01F 5/048; B01F 5/0483; B01F 5/0485; B01F 5/0486; B01F 15/0223; B01F 15/0224; B01F 15/0243; B01F 2003/005; B01F 2005/0005; B01F 2005/0022; B01F 2005/0034; B01F 5/0275; B01F 5/0476; G01N 1/2035; G01N 2001/2064; G01N 1/38; Y10T 137/85978
USPC .................... 366/162.4, 165.5, 178.2, 173.2
See application file for complete search history.

(56) References Cited

U.S. PATENT DOCUMENTS

| | | | | |
|---|---|---|---|---|
| 145,538 | A | * | 12/1873 | Stoddart ................. 261/124 |
| 2,563,002 | A | * | 8/1951 | Bissell .................. B01F 5/0415 |
| | | | | 137/888 |

(Continued)

OTHER PUBLICATIONS

Brochure for Jiskoot(TM) Quality Systems JetMix(R), two pages, published by Cameron International Corporation, Houston, Texas, dated 2011.

*Primary Examiner* — Tony G Soohoo
(74) *Attorney, Agent, or Firm* — Eubanks PLLC

(57) ABSTRACT

An apparatus for mixing fluids within a pipe is provided. In one embodiment, the apparatus includes a fluid mixing device with a pipe having a pipe wall and an axial bore for conveying fluids through the pipe. The fluid mixing device also includes a sleeve disposed about the pipe and a cavity provided between an exterior surface of the pipe and an interior surface of the sleeve. The cavity and the axial bore of the pipe are in fluid communication with one another via an opening through the pipe wall. Additional systems, devices, and methods are also disclosed.

21 Claims, 3 Drawing Sheets

(51) Int. Cl.
*G01N 1/28* (2006.01)
*G01N 1/38* (2006.01)
*B01F 5/00* (2006.01)
*B01F 15/02* (2006.01)

(56) References Cited

U.S. PATENT DOCUMENTS

| | | | | |
|---|---|---|---|---|
| 2,820,620 A * | 1/1958 | Anderson | ............... | F28C 3/06 122/31.1 |
| 3,219,483 A * | 11/1965 | Goos et al. | ............... | B01F 5/0475 127/28 |
| 3,332,442 A * | 7/1967 | Reed | ............... | B01F 5/045 137/896 |
| 3,409,274 A * | 11/1968 | Lawton | ............... | B01F 5/0475 261/76 |
| 3,698,430 A * | 10/1972 | Van Gasselt | ............... | B01F 5/0475 366/181.5 |
| 3,872,217 A * | 3/1975 | Merz | ............... | B01F 5/0471 422/224 |
| 3,913,617 A * | 10/1975 | van Laar | ............... | B01F 5/0471 137/599.01 |
| 4,110,973 A * | 9/1978 | Haeflich | ............... | B01F 5/0475 261/118 |
| 4,212,544 A * | 7/1980 | Crosby | ............... | B01F 5/02 366/167.1 |
| 4,230,410 A * | 10/1980 | Kastl | ............... | B01F 5/0475 366/178.2 |
| 4,285,367 A * | 8/1981 | Nommensen | ............... | B01F 5/0415 137/888 |
| 4,307,620 A | 12/1981 | Jiskoot | | |
| 4,398,827 A * | 8/1983 | Dietrich | ............... | B01F 5/0057 239/404 |
| 4,415,368 A * | 11/1983 | Kroon | ............... | B01F 5/0471 134/10 |
| 4,474,477 A * | 10/1984 | Smith | ............... | B01F 5/0475 261/118 |
| 4,625,916 A * | 12/1986 | Nieuwkamp | ............... | B01F 5/0475 239/431 |
| 4,656,001 A * | 4/1987 | Roger | ............... | B01F 5/0475 137/13 |
| 4,743,405 A * | 5/1988 | Durao | ............... | B01F 5/0475 261/76 |
| 4,886,369 A * | 12/1989 | Hankison | ............... | B01F 5/0403 366/165.5 |
| 4,938,606 A * | 7/1990 | Kunz | ............... | B01F 3/0807 123/25 E |
| 5,004,484 A * | 4/1991 | Stirling | ............... | B01D 19/0005 210/188 |
| 5,046,855 A * | 9/1991 | Allen | ............... | B01F 13/10 137/605 |
| 5,103,908 A * | 4/1992 | Allen | ............... | B01F 3/04836 166/285 |
| 5,131,757 A * | 7/1992 | Smith | ............... | B01F 5/0475 261/118 |
| 5,240,650 A * | 8/1993 | Wiederhold | ............... | B01F 5/0475 261/76 |
| 5,810,474 A * | 9/1998 | Hidalgo | ............... | B01F 5/0683 366/119 |
| 5,845,993 A * | 12/1998 | Shirtum | ............... | B01F 3/04262 366/101 |
| 5,935,490 A * | 8/1999 | Archbold | ............... | B01F 3/0446 261/76 |
| 6,237,897 B1 * | 5/2001 | Marina | ............... | B01F 5/0413 137/855 |
| 6,290,917 B1 * | 9/2001 | Yamamoto | ............... | B01F 5/0057 261/76 |
| 6,453,926 B1 * | 9/2002 | Baker | ............... | B01F 5/0473 137/3 |
| 6,623,154 B1 * | 9/2003 | Garcia | ............... | B01F 5/0415 137/888 |
| 6,767,007 B2 * | 7/2004 | Luman | ............... | B01F 3/0446 261/76 |
| 8,827,544 B2 | 9/2014 | Bachman et al. | | |
| 9,700,855 B2 | 7/2017 | Bachman et al. | | |
| 2002/0096792 A1 * | 7/2002 | Valela | ............... | B01F 3/0446 261/4 |
| 2003/0081493 A1 * | 5/2003 | Allen | ............... | B01F 5/02 366/10 |
| 2003/0178732 A1 * | 9/2003 | Luman | ............... | B01F 3/0446 261/79.2 |
| 2004/0190368 A1 * | 9/2004 | Allen | ............... | B01F 5/0475 366/152.1 |
| 2004/0231586 A1 * | 11/2004 | Dugue | ............... | B01F 5/0475 118/715 |
| 2006/0060679 A1 * | 3/2006 | Miller | ............... | B01F 5/0471 239/584 |
| 2008/0087348 A1 * | 4/2008 | Gillis | ............... | B01F 5/0475 137/896 |
| 2008/0159065 A1 * | 7/2008 | Ding | ............... | B01F 5/0475 366/162.4 |
| 2009/0201761 A1 * | 8/2009 | Matsuno | ............... | B01F 3/0446 366/165.2 |
| 2010/0085833 A1 * | 4/2010 | Zaiser | ............... | B01F 5/0475 366/107 |
| 2010/0137634 A1 * | 6/2010 | Ding | ............... | B01F 5/0473 560/347 |
| 2010/0149906 A1 | 6/2010 | Burns, II | | |
| 2013/0036800 A1 * | 2/2013 | Mohajer | ............... | G01N 1/2035 73/61.59 |
| 2013/0079550 A1 * | 3/2013 | Gillis | ............... | B01F 5/048 560/348 |
| 2016/0346744 A1 * | 12/2016 | Jiskoot | ............... | B01F 5/0275 |

* cited by examiner

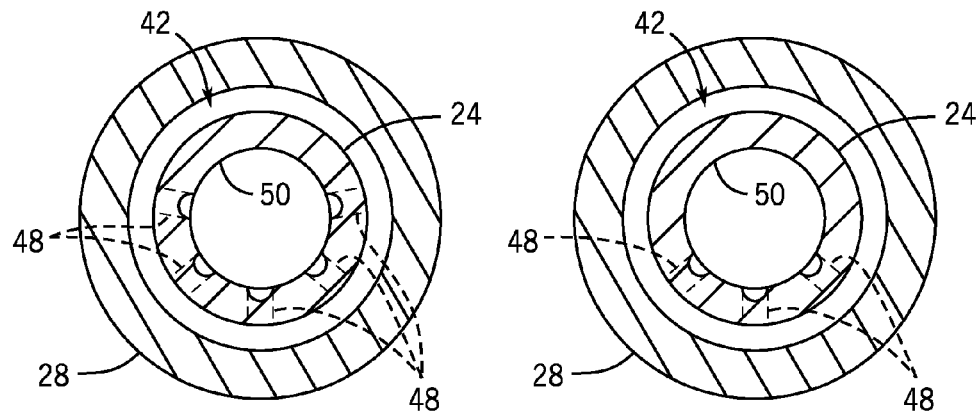
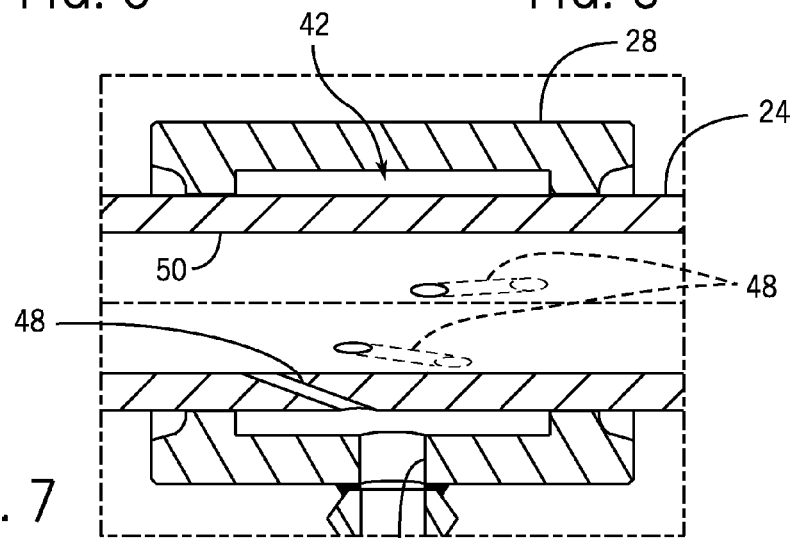
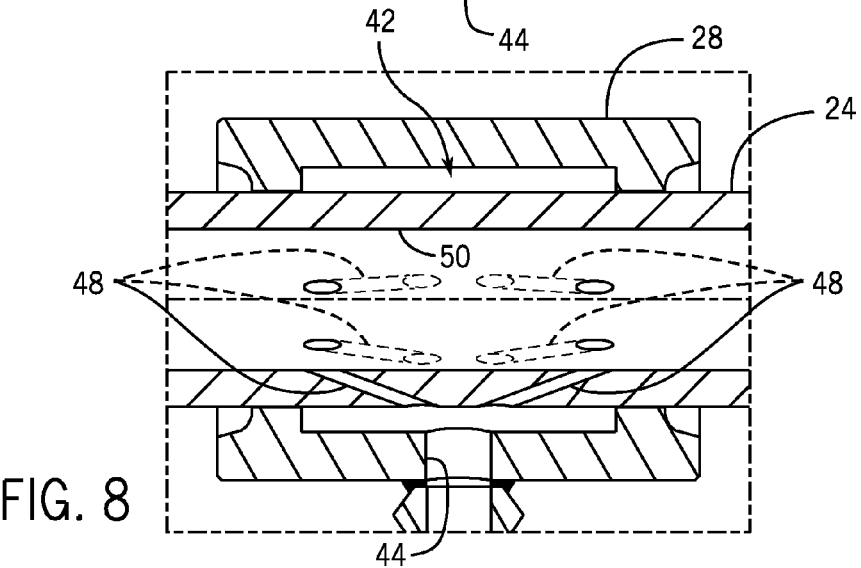

APPARATUS FOR MIXING OF FLUIDS FLOWING THROUGH A CONDUIT

BACKGROUND

This section is intended to introduce the reader to various aspects of art that may be related to various aspects of the presently described embodiments. This discussion is believed to be helpful in providing the reader with background information to facilitate a better understanding of the various aspects of the present embodiments. Accordingly, it should be understood that these statements are to be read in this light, and not as admissions of prior art.

In order to meet consumer and industrial demand for natural resources, companies often invest significant amounts of time and money in finding and extracting oil, natural gas, and other subterranean resources from the earth. Particularly, once desired subterranean resources such as oil or natural gas are discovered, drilling and production systems are often used to access and extract the resources. These systems may be located onshore or offshore depending on the locations of the desired resources. Once extracted, the resources are often transported via pipelines to desired locations, such as refineries.

Pipelines often convey multiple fluids simultaneously. For instance, flowing oil, water, and gas can be present in different proportions at a given location in the pipeline. In such cases, the fluid is often referred to as a multiphase fluid that includes individual phases of oil, water, and gas. Particulates, such as sand or sediment, may also be carried by the multiphase fluid. The fluid traveling through the pipeline can be analyzed to determine characteristics of the fluid. Such analysis can be performed in situ at the pipeline or on samples collected from the pipeline for future analysis, such as in a laboratory. Determined characteristics of fluid flowing through the pipeline may be used in various manners, such as to facilitate custody transfer of hydrocarbon fluids, auditing, taxation, and quality management.

SUMMARY

Certain aspects of some embodiments disclosed herein are set forth below. It should be understood that these aspects are presented merely to provide the reader with a brief summary of certain forms the invention might take and that these aspects are not intended to limit the scope of the invention. Indeed, the invention may encompass a variety of aspects that may not be set forth below.

Embodiments of the present disclosure generally relate to the mixing of fluids flowing through conduits. In certain embodiments, an apparatus includes a device that injects a mixing fluid into a pipe to agitate and mix fluid that is flowing through the pipe. In at least some instances, the mixing fluid is drawn from the pipe and then returned back into the pipe to mix the flowing fluid. The fluid mixing device can include a sleeve positioned about the pipe. Mixing fluid is pumped into a cavity within the sleeve and is routed from the cavity into the pipe as fluid jets through openings in the wall of the pipe.

Various refinements of the features noted above may exist in relation to various aspects of the present embodiments. Further features may also be incorporated in these various aspects. These refinements and additional features may exist individually or in any combination. For instance, various features discussed below in relation to one or more of the illustrated embodiments may be incorporated into any of the above-described aspects of the present disclosure alone or in any combination. Again, the brief summary presented above is intended only to familiarize the reader with certain aspects and contexts of some embodiments without limitation to the claimed subject matter.

BRIEF DESCRIPTION OF THE DRAWINGS

These and other features, aspects, and advantages of certain embodiments will become better understood when the following detailed description is read with reference to the accompanying drawings in which like characters represent like parts throughout the drawings, wherein:

FIG. 5 is a cross-section of the fluid mixing device of FIG. 2, showing five openings through which fluid jets may enter the bore of the pipe from the internal cavity to mix fluids passing through the bore, in accordance with one embodiment;

FIG. 6 is a cross-section of a fluid mixing device similar to that of FIG. 2, but in which the fluid mixing device includes fewer openings connecting the internal cavity within the sleeve to the bore inside the pipe, in accordance with one embodiment;

FIG. 7 is a detail view of a portion of a fluid mixing device having openings in the pipe wall that connect the internal cavity within the sleeve to the bore inside the pipe and that are axially offset so as to provide fluid mixing jets at different axial locations within the bore in accordance with one embodiment; and FIG. 8 is a detail view of a portion of a fluid mixing device having two sets of openings that connect the internal cavity within the sleeve to the bore inside the pipe, with the two sets of openings axially offset from one another and the openings of each set axially aligned with the other openings of that set, in accordance with one embodiment.

DETAILED DESCRIPTION OF SPECIFIC EMBODIMENTS

One or more specific embodiments of the present disclosure will be described below. In an effort to provide a concise description of these embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments, the articles "a," "an," "the," and "said" are intended to mean that there are one or more of the elements. The terms "comprising," "including," and "having" are intended to be inclusive and mean that there may be additional elements other than the listed elements. Moreover, any use of "top," "bottom," "above," "below," other directional terms, and variations of these terms is made for convenience, but does not require any particular orientation of the components.

Figure 1:
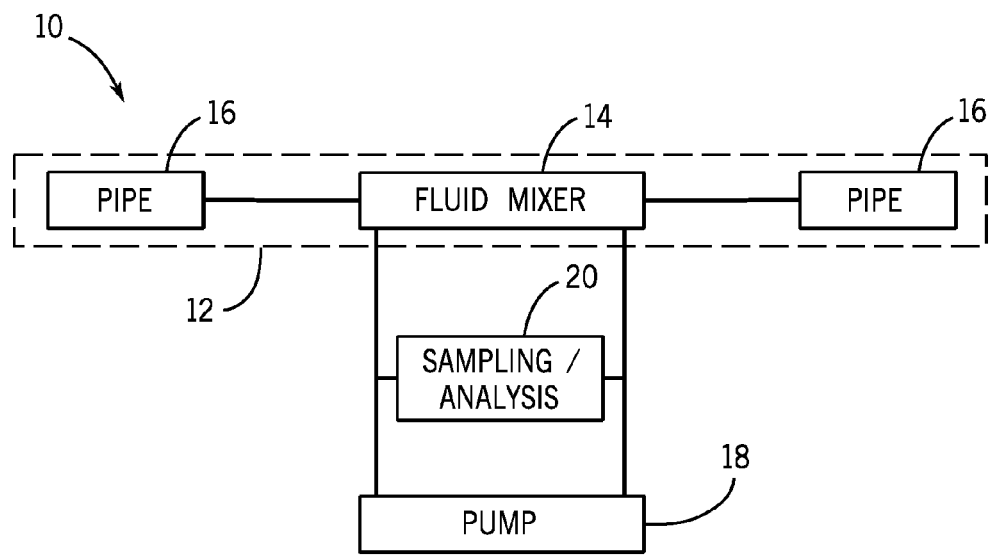
FIG. 1 is a block diagram representing components of an apparatus for conveying fluids through a conduit and mixing the fluids within the conduit in accordance with certain embodiments of the present disclosure.

Turning now to the drawings, an apparatus 10 in which fluids can be mixed is generally illustrated in FIG. 1 by way of example. The apparatus 10 includes a portion 12 of a fluid conduit that has a fluid mixing device 14 installed between pipes 16, so that fluids flowing through the portion 12 of the fluid conduit pass between the pipes 16 through the fluid mixing device 14. In at least some embodiments, the fluid conduit having the fluid mixing device 14 is a pipeline or some other fluid transfer line conveying a non-homogeneous fluid (e.g., a multiphase fluid or a single-phase mixture of different fluids).

A pump 18 is connected in fluid communication with the fluid mixing device 14. In at least some embodiments, the pump 18 draws fluid from the fluid mixing device 14 and then pumps that drawn fluid back into the fluid mixing device 14. As described in greater detail below, the fluid returned to the fluid mixing device 14 by the pump 18 can be injected into a mixing chamber as fluid jets. These jets mix the fluid passing between the pipes 16 through the fluid mixing device 14. In other embodiments, the pump 18 draws fluid from some other source (e.g., a fluid having a different grade than that flowing into the mixing device 14 from a pipe 16), rather than from the mixing device 14, and injects that fluid to mix the fluid flowing through the device 14.

As depicted in FIG. 1, the apparatus 10 also includes sampling and analysis systems 20. For example, fluid drawn from the fluid mixing device 14 by the pump 18 can be analyzed to determine various fluid properties, and samples of the fluid can be retained for later analysis. The systems 20 can include a density meter, a viscosity meter, a flow meter, a water-in-oil meter, pressure and temperature compensation devices, fluid sample chambers, or any other suitable devices.

The systems 20 are generally shown in parallel with the pump 18 in FIG. 1, and can receive fluid from a return loop through which fluid drawn from the fluid mixing device 14 by the pump 18 passes before being returned to the fluid mixing device 14. In other embodiments, however, the apparatus 10 could also or instead include sampling or analysis systems 20 in series with the pump 18 or at another location (e.g., downstream from the fluid mixing device 14), or such systems 20 could be omitted.

Those skilled in the art will appreciate that multiphase fluids can flow through a pipeline under various flow regimes. For example, due to gravity, a multiphase fluid passing through a horizontal pipe may have a stratified flow in which, generally, water flows along the bottom of the pipe, oil flows through the pipe above the water, and gas flows over the oil in the top of the pipe. Sediment or other particulates can be carried by any of the individual phases but may be concentrated at the bottom of the pipe. In other instances, multiphase fluids can pass through a pipe in a different manner, such as in a plug flow, a slug flow, an annular flow, or a wavy flow.

In at least some embodiments, the pump 18 energizes a mixing fluid and injects that mixing fluid into the device 14 to disrupt the flow pattern of the multiphase fluid and better mix its individual phases with one another. The device 14 can be used to mix two-phase flows (e.g., water and oil) in some embodiments, but could also be used to mix other multiphase flows (e.g., water, oil, and gas). This mixture can then be analyzed or sampled to determine characteristics of the multiphase fluid. If the multiphase fluid were not sufficiently mixed, the composition of a sample acquired downstream may not be representative of the composition of the multiphase fluid as a whole. For example, if water and oil flowing through a pipe were not well mixed, fluid drawn from a sampling tap at the bottom of the pipe may have a higher proportion of water and a lower proportion of oil than is present within the pipe itself. With mixing by the device 14, however, the individual phases can be more evenly distributed within a cross-section of the device 14, which facilitates collection or analysis of a representative sample of the fluid mixture downstream from the mixing location.

Figure 2:
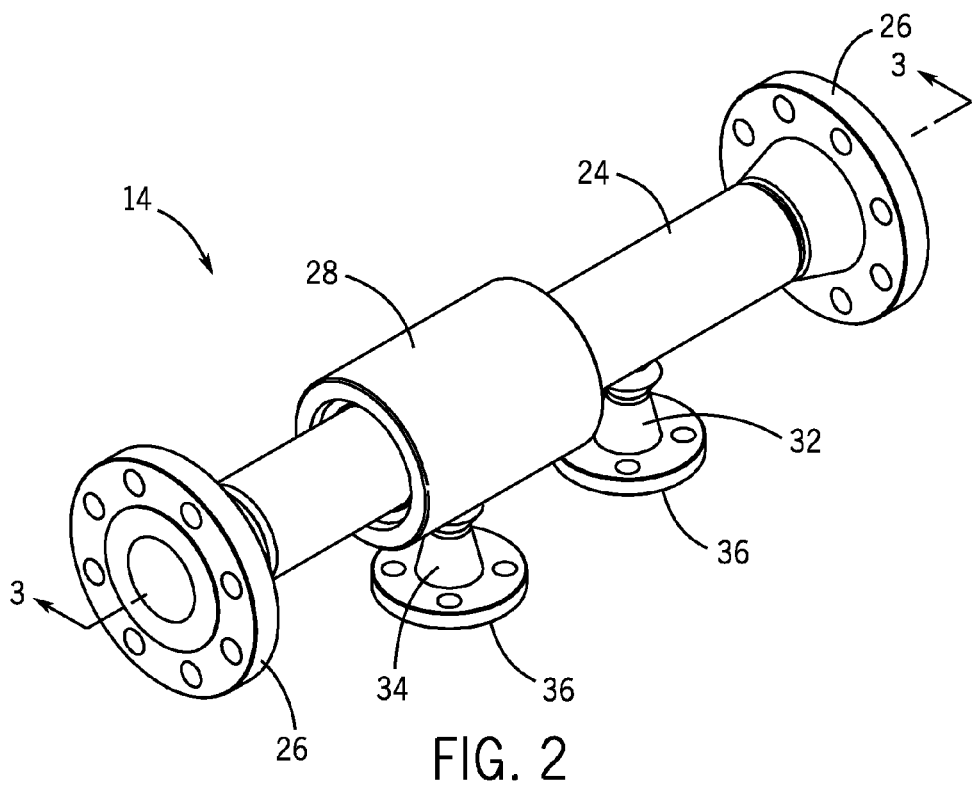
FIG. 2 is a perspective view of a fluid mixing device that includes an outer sleeve disposed about a pipe and that may be used to mix fluids flowing through a conduit in accordance with one embodiment.
Figure 3:
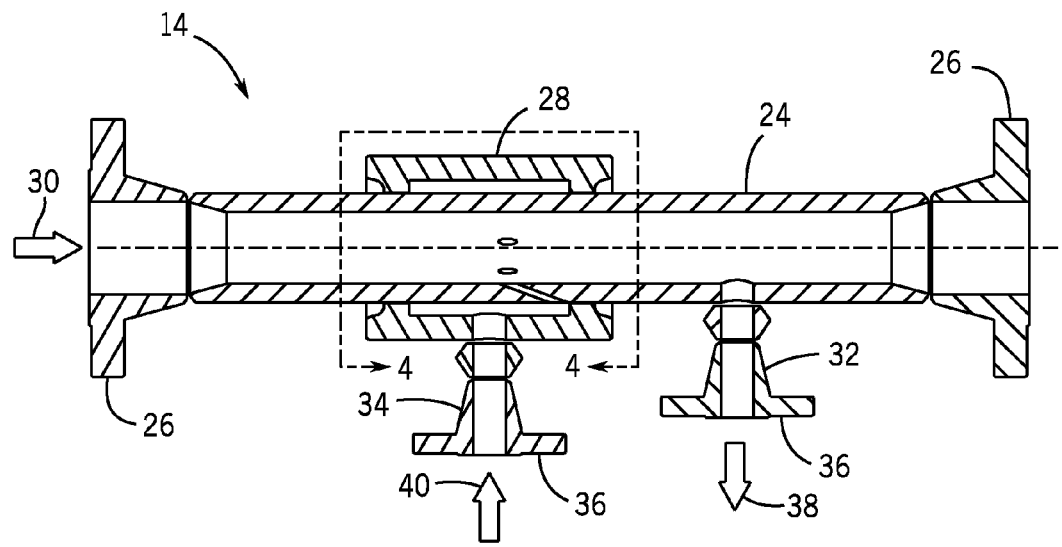
FIG. 3 is a cross-section of the fluid mixing device of FIG. 2 showing an internal cavity that is within the outer sleeve and that is connected in fluid communication with the axial bore of the pipe via openings through the wall of the pipe in accordance with one embodiment.

One example of the fluid mixing device 14 is depicted in FIGS. 2 and 3. In this embodiment, the fluid mixing device 14 includes a conduit in the form of a pipe 24 for conveying fluid between other pipes 16. The pipe 24 includes flanged ends 26 that can be coupled to mating flanges of the pipes 16 to facilitate installation of the fluid mixing device 14 in a pipeline or other fluid conduit. In at least some embodiments, the fluid mixing device 14 is a spool section that is installed directly into a pipeline so as to be positioned in-line with other pipes 16 of the pipeline and the pipe 24 can have the same inner diameter as the adjoining pipes 16. The fluid mixing device 14 can be used in various contexts, such as in pipelines for conveying shale liquids with high Reid vapor pressure or in offshore allocation pipelines to name just two examples. The pipe 24 can be installed in any desired orientation, such as horizontally in some embodiments and vertically in others.

The depicted fluid mixing device 14 includes a sleeve 28 positioned about the pipe 24. As described in greater detail below, the sleeve 28 encloses a cavity between an exterior surface of the pipe 24 and an interior surface of the sleeve 28. In at least some embodiments, the sleeve 28 is concentric with the pipe 24 and the enclosed cavity is an annular cavity. The sleeve 28 can be coupled to the pipe 24 in any suitable manner. For instance, the ends of the sleeve 28 are welded to the exterior of the pipe 24 in one embodiment.

Fluid entering the pipe 24 (e.g., from an upstream pipe 16), as generally represented by arrow 30, can be mixed by the fluid mixing device 14 as it flows through the pipe 24 within the sleeve 28. More specifically, the presently depicted fluid mixing device 14 includes an outlet tap 32 connected to the pipe 24 and an inlet tap 34 connected to the sleeve 28. The outlet tap 32 and the inlet tap 34 may be connected to a fluid return loop including the pump 18, as described above. Flanges 36 on these taps 32 and 34 facilitate coupling to flanged pipes of the fluid return loop. In one embodiment the pipe 24 has a three-inch inner diameter and the outlet and inlet taps 32 and 34 each have a one-inch diameter, but the present techniques can be used with pipes and taps having other diameters.

In operation, the pump 18 draws fluid out of the pipe 24 via the outlet tap 32 (as generally represented by arrow 38) and pumps drawn fluid back into the fluid mixing device 14 through the inlet tap 34 coupled at the sleeve 28 (as generally represented by arrow 40). The fluid mixing device 14 is depicted in FIG. 3 as having the outlet tap 32 downstream from the inlet tap 34, but the outlet tap 32 could instead be provided upstream of the inlet tap 34. Further, the outlet tap 32 could be connected elsewhere in the fluid conduit in which the fluid mixing device 14 is installed (e.g., to a pipe 16 instead of the pipe 24), or the mixing fluid injected into the pipe 24 may be drawn from some other source.

The fluid pumped back into the fluid mixing device 14 through the inlet tap 34 is injected into the fluid that is flowing through the pipe 24. The injected fluid agitates the flowing fluid and causes the contents of the pipe (e.g., the different phases of a multiphase fluid, any sediment or other particles, and the injected fluid) to mix with one another. For example, in the case of a multiphase fluid (e.g., a two-phase fluid) including oil floating over the top of water in the pipe 24, the injected fluid can commingle the oil and the water into a substantially uniform mixture. This, in turn, allows extraction of a representative sample of the mixture for analysis (e.g., via the outlet tap 32 or at some other location downstream from the inlet tap 34).

Figure 4:
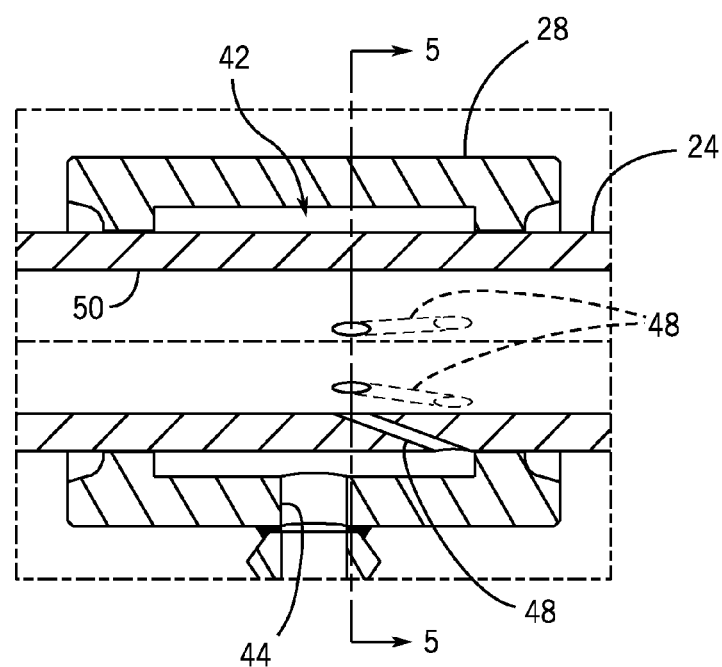
FIG. 4 is a detail view of the internal cavity connected to the bore of the pipe by the openings through the pipe wall.

As shown in greater detail in FIG. 4, fluid returned to the fluid mixing device 14 through the inlet tap 34 can be pumped into a cavity 42 through a port 44 in the sleeve 28. The cavity 42 is enclosed between an interior surface of the sleeve 28 and an exterior surface of the pipe 24. The wall of the pipe 24 includes ducts or other openings 48 that connect the cavity 42 in fluid communication with the axial bore 50 of the pipe 24. The fluid returned to the fluid mixing device 14 via the inlet port 44 pressurizes the cavity 42, causing fluid in the cavity 42 to jet into the bore 50 through the openings 48. Inside the bore 50, which may also be referred to as a mixing chamber, these jets mix the multiphase fluid passing through the pipe 24 between the pipes 16.

Rather than having a nozzle extending into the bore 50 for injecting the returned fluid, the openings 48 formed in the pipe wall allow the fluid returned to the fluid mixing device 14 to be routed directly into the bore 50 without a nozzle (or any other structure) extending into the bore 50. Fluid can also be drawn out through the outlet tap 32 without a probe or other structure extending into the bore 50. In small diameter pipes (i.e., pipes with an inner diameter of no more than six inches), such structures extending into the bore 50 for drawing fluid from or returning fluid to the pipe 24 could cause an undesirable pressure drop in the fluid. Accordingly, in at least some embodiments the fluid mixing device 14 does not include any nozzles, probes, or other structures extending into the bore 50 for drawing fluid from or injecting fluid into the pipe 24. But in other instances, such as with larger pipelines, a probe could be inserted into the pipe 24 or a pipe 16 (e.g., at the outlet tap 32) to draw fluid from closer to the center of the flow.

In at least some embodiments, the multiphase fluid mixed by the fluid jets from the openings 48 is then analyzed downstream of the openings 48, such as by analyzing a portion of the mixed fluid drawn through the outlet tap 32. The mixing of the fluid upstream of the point of analysis can be performed to ensure that the portion of the fluid to be analyzed is representative of the multiphase fluid as a whole. More specifically, the fluid can be mixed in the pipe 24 to ensure that the portion of the fluid drawn through the outlet tap 32 has proportions of individual phases (e.g., of oil and water) that do not meaningfully differ from those in the pipe 24 itself.

The size, shape, number, and arrangement of the openings 48 through the wall of the pipe 24 can be varied between different embodiments. The features of the openings 48 can be chosen based on the diameter of the pipe 24, the orientation of the pipe 24 (e.g., for horizontal or vertical flow), the characteristics of fluid expected to be mixed within the pipe 24 (e.g., viscosity, density, phase fractions, or amount of particulates), or operating characteristics of the pump 18, to name but a few examples. Although the openings 48 could be provided radially through the wall of the pipe 24 in other embodiments, in FIG. 4 the openings 48 are shown as being formed at an angle through the wall (i.e., the axis of each opening 48 is not perpendicular to the central axis of the bore 50). Moreover, each of the openings 48 could be formed at the same angle (as generally shown in FIG. 4). Alternatively, at least some of the openings 48 could be formed at angles that differ from one another. Still further, the dimensions of each of the openings 48 may be identical to one another or may differ.

In FIG. 5, a cross-section of the mixing device 14 of FIG. 4 shows five openings 48 through the wall of the pipe 24 for routing mixing fluid from the cavity 42 into the bore 50. In other embodiments, the number of openings 48 may differ. In FIG. 6, for instance, the fluid device 14 is depicted as having only three openings 48 for mixing fluid jets to enter the bore 50. But in still other embodiments, the fluid device 14 could have a single opening 48 or some other number of openings 48.

Still further, the openings 48 of the fluid mixing device 14 are shown in FIGS. 4 and 5 as having interior ends (at the interior of the pipe wall) that are axially aligned with one another. This allows the mixing fluid to enter the bore 50 through the openings 48 at the same axial location in the pipe 24. In other embodiments, however, the fluid mixing device 14 includes openings 48 that are axially offset from one another. For example, in FIG. 7 the openings 48 have interior ends positioned at different axial locations along the pipe wall.

By way of further example, a pipe 24 could have sets of openings 48 axially offset from one another. As depicted in FIG. 8, the pipe 24 includes a first set of openings 48 with interior ends axially aligned with one another at a first axial location along the pipe 24. The pipe 24 also includes a second set of openings 48 with interior ends axially aligned with one another, but at a second axial location downstream from the first axial location. FIG. 8 further shows the first set of openings 48 angled away from the direction of flow through the bore 50, while the second set of openings 48 is angled toward the direction of flow through the bore 50. The angles of the first and second sets of openings 48 can be equal in magnitude, but differ in direction with respect to a normal to the surface of the pipe 24.

In a further embodiment, multiple mixing devices 14 with differing characteristics could be installed in series in a pipeline (e.g., with pipes 16). For instance, the configuration of the openings 48 (e.g., size, shape, quantity, or orientation) can differ between the multiple mixing devices. This allows selection of different mixing devices 14 to control mixing of the multiphase or other fluid in the pipeline based on a characteristic of the fluid, such as flow rate or fluid properties.

While the aspects of the present disclosure may be susceptible to various modifications and alternative forms, specific embodiments have been shown by way of example in the drawings and have been described in detail herein. But it should be understood that the invention is not intended to be limited to the particular forms disclosed. Rather, the invention is to cover all modifications, equivalents, and alternatives falling within the spirit and scope of the invention as defined by the following appended claims.

The invention claimed is:

1. An apparatus comprising:
a fluid mixing device including:
a pipe having a pipe wall and an axial bore that extends from an inlet of the pipe to an outlet of the pipe for conveying fluids through the pipe from the inlet of the pipe to the outlet of the pipe;
a sleeve disposed about the pipe;
a cavity provided between an exterior surface of the pipe and an interior surface of the sleeve, wherein the cavity and the axial bore of the pipe are in fluid communication with one another via an opening through the pipe wall, and the opening through the pipe wall is located between the inlet of the pipe and the outlet of the pipe;
an outlet tap connected to the pipe at a location between the inlet of the pipe and the outlet of the pipe so as to receive, through the pipe wall from the axial bore, a portion of the fluids conveyed through the pipe; and
an inlet tap connected to the sleeve, wherein the outlet tap is positioned downstream of the inlet tap.

2. The apparatus of claim 1, wherein the outlet tap is in fluid communication with the inlet tap via a fluid return loop including an analysis system for analyzing the portion of the fluids received through the outlet tap.

3. The apparatus of claim 1, comprising a pump coupled in fluid communication between the outlet tap and the inlet tap, wherein the pump is configured to draw the portion of the fluids conveyed through the pipe from the axial bore via the outlet tap and to pump the portion of the fluids drawn from the axial bore into the cavity via the inlet tap, and the opening through the pipe wall is configured to jet the portion of the fluids from the cavity into the axial bore to mix the fluids conveyed through the pipe.

4. The apparatus of claim 1, wherein the cavity and the axial bore of the pipe are in fluid communication with one another via multiple openings through the pipe wall.

5. The apparatus of claim 4, wherein the multiple openings are angled through the pipe wall.

6. The apparatus of claim 5, wherein each of the multiple openings is provided at a same angle through the pipe wall.

7. The apparatus of claim 5, wherein one of the multiple openings is angled toward the direction of flow through the axial bore and another of the multiple openings is angled away from the direction of flow through the axial bore.

8. The apparatus of claim 4, wherein each of the multiple openings has dimensions identical to the other openings of the multiple openings.

9. The apparatus of claim 4, wherein the multiple openings include interior ends at the interior of the pipe wall that are axially aligned with one another.

10. The apparatus of claim 4, wherein the multiple openings include at least two openings having interior ends at the interior of the pipe wall that are axially offset from one another.

11. The apparatus of claim 1, wherein the cavity is an annular cavity.

12. The apparatus of claim 1, wherein the pipe of the fluid mixing device is connected in-line with other pipes of a pipeline.

13. An apparatus comprising:
a conduit having a bore for conveying a multiphase fluid, the conduit extending from an inlet of the conduit to an outlet of the conduit and including a plurality of ducts extending through a wall of the conduit between the inlet of the conduit and the outlet of the conduit; and
an external pump that is outside the conduit and is coupled in fluid communication with the plurality of ducts so as to enable a mixing fluid to be pumped into the bore by the external pump through the wall via the plurality of ducts, wherein the external pump is coupled in fluid communication with the conduit via an outlet tap positioned between the inlet of the conduit and the outlet of the conduit to draw a portion of the multiphase fluid out of the bore through the outlet tap and then pump the portion of the multiphase fluid back into the bore through the wall via the plurality of ducts between the inlet of the conduit and the outlet of the conduit as the mixing fluid.

14. The apparatus of claim 13, comprising an enclosed cavity along an outside of the conduit, wherein the external pump is coupled in fluid communication with the plurality of ducts via the enclosed cavity.

15. The apparatus of claim 14, comprising a sleeve positioned about the conduit such that the enclosed cavity lies between the outside of the conduit and an inside of the sleeve.

16. A method comprising:
routing a multiphase fluid into a pipe of a fluid mixing device, the pipe having a pipe wall and an axial bore that extends from an inlet of the pipe to an outlet of the pipe for conveying the multiphase fluid through the pipe from the inlet of the pipe to the outlet of the pipe, wherein the fluid mixing device also includes: a sleeve disposed about the pipe; a cavity provided between an exterior surface of the pipe and an interior surface of the sleeve, wherein the cavity and the axial bore of the pipe are in fluid communication with one another via openings through the pipe wall, and the opening through the pipe wall is located between the inlet of the pipe and the outlet of the pipe; an outlet tap connected to the pipe at a location between the inlet of the pipe and the outlet of the pipe so as to receive, through the pipe wall from the axial bore, a portion of the fluids conveyed through the pipe; and an inlet tap connected to the sleeve, wherein the outlet tap is positioned downstream of the inlet tap; and
jetting a mixing fluid directly into the pipe via the openings through the pipe wall to mix components of the multiphase fluid with one another.

17. The method of claim 16, comprising routing the multiphase fluid through the axial bore of the pipe and jetting the mixing fluid directly into the axial bore without obstructing flow of the multiphase fluid with a structure extending into the axial bore.

18. The method of claim 16, comprising pumping the mixing fluid into the cavity, wherein jetting the mixing fluid directly into the pipe includes jetting the mixing fluid from the cavity into the pipe.

19. The method of claim 16, comprising drawing the mixing fluid from the multiphase fluid routed into the pipe.

20. The method of claim 19, wherein drawing the mixing fluid from the multiphase fluid routed into the pipe includes drawing the mixing fluid from the multiphase fluid via the outlet tap downstream of a location at which the mixing fluid is jetted into the pipe through the openings in the wall.

21. The method of claim 16, comprising:
routing the multiphase fluid through a series of fluid mixing devices including the fluid mixing device and one or more additional fluid mixing devices having a pipe for receiving the multiphase fluid and openings through a pipe wall of the pipe to mix components of the multiphase fluid with one another, wherein the configuration of the openings through the pipe wall differ between the fluid mixing device and the one or more additional fluid mixing devices; and selecting the fluid mixing device for mixing the components based on a characteristic of the multiphase fluid.

\* \* \* \* \*